US008070737B2

(12) United States Patent
Cline et al.

(10) Patent No.: US 8,070,737 B2
(45) Date of Patent: Dec. 6, 2011

(54) SEAL FOR CONTROLLED EVACUATION OSTOMY APPLIANCE

(75) Inventors: John B. Cline, New Brunswick, NJ (US); Christopher C. Gregory, Newton, PA (US); Geraint Davies, Cambridge (GB); Alan Cucknell, Cambridge (GB); Julian Scarfe, Cambridge (GB); Pete Cauwood, Cambridge (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 830 days.

(21) Appl. No.: 11/619,460

(22) Filed: Jan. 3, 2007

(65) Prior Publication Data

US 2007/0191794 A1 Aug. 16, 2007

Related U.S. Application Data

(60) Provisional application No. 60/756,915, filed on Jan. 6, 2006.

(51) Int. Cl.
*A61F 5/44* (2006.01)

(52) U.S. Cl. ........ 604/338; 604/332; 604/333; 604/334; 604/335; 604/336; 604/337; 604/339; 604/340; 604/341; 604/342; 604/343; 604/344; 604/345; 604/355; 604/277; 600/30; 600/31; 600/32; 128/887; 602/13

(58) Field of Classification Search .......... 604/277, 604/332–345, 355; 600/30–32; 128/887; 602/13
See application file for complete search history.

(56) References Cited

U.S. PATENT DOCUMENTS

| | | | | |
|---|---|---|---|---|
| 4,596,566 A | * | 6/1986 | Kay | 604/343 |
| 4,723,952 A | | 2/1988 | Esposito | |
| 4,950,223 A | * | 8/1990 | Silvanov | 600/32 |
| 4,981,465 A | * | 1/1991 | Ballan et al. | 600/32 |
| 6,659,988 B1 | * | 12/2003 | Steer et al. | 604/333 |
| 2003/0181879 A1 | * | 9/2003 | Mulhauser et al. | 604/332 |
| 2006/0058577 A1 | * | 3/2006 | Davies et al. | 600/32 |
| 2007/0123832 A1 | * | 5/2007 | Cline et al. | 604/335 |

FOREIGN PATENT DOCUMENTS

| | | | |
|---|---|---|---|
| EP | 1348412 | | 10/2003 |
| EP | 1637100 | | 3/2006 |
| EP | 1774931 | | 4/2007 |
| WO | WO 90/07311 | * | 7/1990 |

* cited by examiner

*Primary Examiner* — Tatyana Zalukaeva
*Assistant Examiner* — Ginger T Chapman
(74) *Attorney, Agent, or Firm* — Stuart E. Krieger

(57) ABSTRACT

A controlled evacuation ostomy appliance comprises a membrane that is urged into sealing engagement with a stoma, by the generation of radial tension in the membrane. A tensioning device applies tension, with respect to the stoma, at one or more positions that are (i) outboard of the periphery of the projecting portion of the stoma, and/or (ii) between the level of the peristomal skin and the level of the most projecting part of the stoma. Tension limiting means are disclosed. The membrane may be gas-permeable to allow flatus to be vented.

16 Claims, 7 Drawing Sheets

SEAL FOR CONTROLLED EVACUATION OSTOMY APPLIANCE

The present invention relates to the field of ostomy appliances, and in particular to such appliances which can be used to control stomal discharge, occasionally referred to as controlled evacuation appliances. One aspect of the invention relates to a seal for such an appliance for blocking the discharge of stool from the stoma.

BACKGROUND TO THE INVENTION

The creation of an ostomy (stoma) is the therapy for many sufferers of diseases or injury of the gastrointestinal or urinary tract. An ostomy is the rerouting of the tract through the abdominal wall to outside the patient's body. Once a stoma has been created, the patient must, usually for the rest of his or her life, use a device worn on the body for capturing or containing the body waste. This has traditionally been done with a bag or pouch attached to the body with adhesive patches or constricting belts. However, the wearing of such a pouch may be an embarrassing experience for some ostomates. A pouch may require changes in a person's public and personal activities.

A controlled evacuation appliance offers the potential benefit to an ostomate of achieving some control over the evacuation of body waste. The appliance is used to block the stoma opening, in order to store the liquid and/or solid stool temporarily inside the tract. The appliance is deactivatable and/or removable manually when the ostomate desires to discharge the stool from the stoma. A structural feature which distinguishes a controlled evacuation appliance from a conventional ostomy pouch is the presence of a stoma seal, for blocking the stoma opening. However, there are many practical and challenging difficulties associated with implementing a cost efficient, yet effective and comfortable stoma seal. It is believed that this is one of the reasons why controlled evacuation appliances have hitherto not found widespread use.

SUMMARY OF THE INVENTION

A first aspect of the invention is to provide a stoma seal for a controlled evacuation device, and to apply tension to the stoma seal. The tension generates a sealing pressure against the stoma.

The tension may be applied from or via one or more positions that include:
  (a) laterally (e.g., radially) outside the periphery of the projecting portion of the stoma, for example, the position(s) completely surround the stoma, and are outboard of the stoma,; and/or
  (b) closer to the peristomal skin than is the most projecting point of the mouth of the stoma, for example, the position(s) are between the level of the most projecting point of the stoma, and the level of the peristomal skin.

A tensioned stoma seal provides an alternative seal design that can achieve a reliable seal, without having to use an inflated seal member.

Additional features and/or aspects of the invention are defined in the claims and or are apparent from the following description. Although certain features have been highlighted above and in the appended claims, claim protection may be sought for any inventive feature and/or idea described herein and/or illustrated in the drawings, whether or not emphasis has been placed thereon.

DETAILED DESCRIPTION OF PREFERRED EMBODIMENTSS

Figure 1:
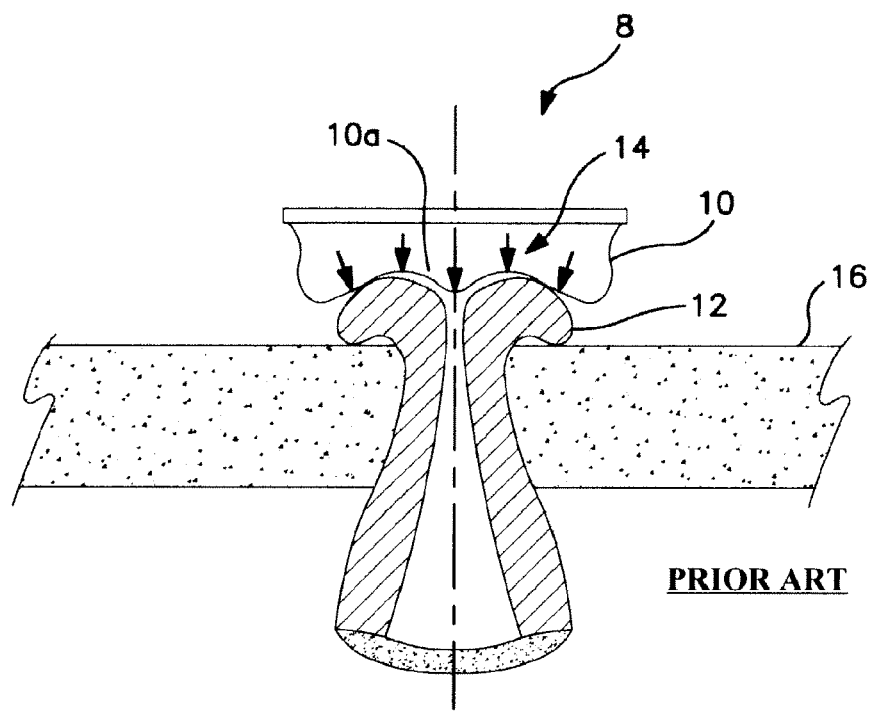
FIG. 1 is a schematic cross sectional view of a controlled evacuation appliance with an inflatable stoma seal.

Referring to FIGS. 1-11, where FIG. 1 shows a prior art embodiment of a controlled evacuation device 8 having a stoma seal in the form of an inflatable bag 10. The internal pressure within the inflatable bag 10 presses a membrane portion 10a of the inflatable bag 10 against a wearer's stoma 12 projecting from the skin surface 16. The sealing pressure against the stoma 12 is generally equal to the internal pressure within the inflatable bag 10. The inflatable bag 10 requires a pump (not shown) to be used to inflate the bag 10 to a desired pressure. Alternatively, the inflatable bag 10 may be pre-inflated during manufacture. Although pre-inflation avoids the need and expense of a separate pump and valve arrangement, pre-inflation has the potential disadvantage of leakage of the inflation fluid by slow diffusion of the inflation fluid through the bag wall material over time. An inflatable bag 10 provides excellent sealing properties when properly designed. The present invention seeks to provide an alternative construction which can achieve effective seal performance without an inflatable bag 10.

Figure 2:
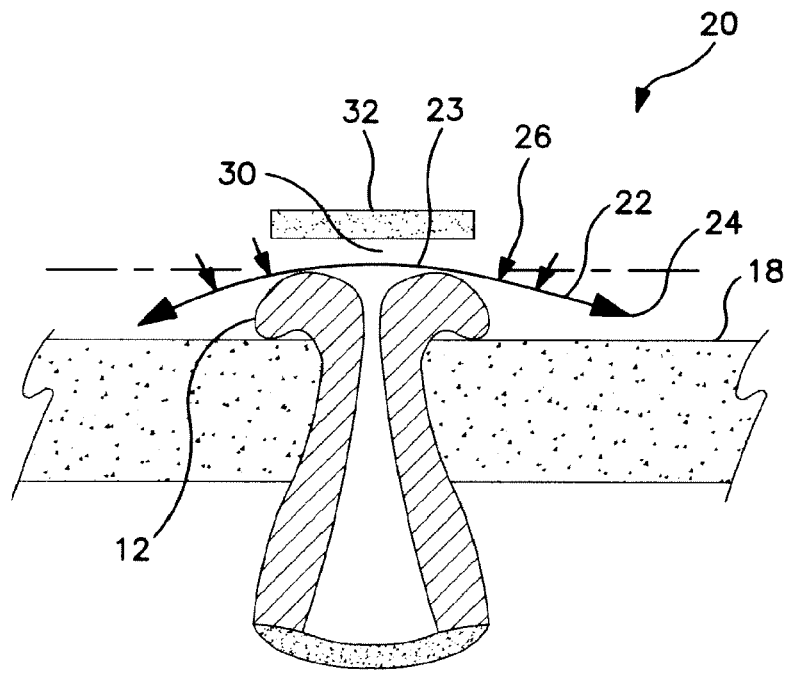
FIG. 2 is a schematic cross sectional view of a controlled evacuation ostomy appliance with a tensioned stoma seal.

Referring to FIG. 2, a controlled evacuation ostomy appliance (or appliance) 20 is illustrated in accordance with the principles of the present invention. The appliance 20 comprises a stoma seal 22 for blocking or occluding the mouth of a wearer's stoma 12, in order to substantially contain fecal matter in the region of the stoma 12. The stoma seal 22 may be inflated or non-inflatable. The stoma seal 22 may, for example, be in the form of a membrane, or a flexible film.

A feature of this embodiment is the application of tension to the stoma seal 22, as indicated by the arrows 24 in FIG. 2. The tension in the stoma seal 22 generates a sealing pressure against the stoma 12, as illustrated by arrows 26 in FIG. 2. The tension is applied from or via one or more positions that may be:

(a) laterally (e.g., radially) outside the periphery of the raised portion of the stoma 12, for example, the position (s) completely surround the stoma 12, and are outboard of the stoma 12; and/or (b) closer to the peristomal skin 18 than is the highest point 23 of the mouth of the stoma 12, for example, in the orientation shown in FIG. 2, the position(s) are below the level of the highest point 23 of the stoma 12 and above the level of the peristomal skin 18.

The tension is applied to draw the stoma seal 22 into a concave configuration around the stoma 12. The stoma seal 22 may be under tension prior to the appliance 20 being fitted to the stoma 12. Alternatively, the stoma seal 22 may be under little or no tension prior to the appliance 20 being fitted to the stoma 12, and the tension is generated by deformation of the stoma seal 22 when pressed against the protruding shape of the stoma 12. The stoma seal 22 may be made of a resilient material, or the stoma seal 22 may be non-resilient.

The use of tension to create the sealing force has certain potential advantages compared to the use of inflation pressure as in the prior art appliance 8 of FIG. 1.

One advantage of the present invention is that the tensioning force is set mechanically without relying on the generation and maintenance of an inflation pressure. Various mechanical tensioning structures to accomplish this according to the present invention are described hereinafter. However, in general, a mechanical tensioning arrangement as provided herein can avoid the need for any inflation pump, leading to a less expensive product; avoid the problems associated with leakage of inflation fluid for a pre-inflated bag; and enable a more robust appliance to be provided which does not require the same delicate handling and storage as a pre-inflated bag.

Also, as illustrated by the arrows 26 in FIG. 2, the tensioning applies a force in an at least partly inward direction from outside the stoma 12. The force is converging and tends to collapse the wall of the stoma 12 inwardly at the mouth, and assist with the desired (temporary) blockage of feces. In contrast, as indicated by the arrows 14 in FIG. 1, the force applied by the inflatable bag 10 acts oppositely, tending to push apart the stoma walls. If the inflatable bag 10 is not carefully designed, such forces could make blockage more difficult and/or less reliable.

Also, in the tensioned stoma seal 22 of FIG. 2, the sealing force applied to the stoma 12 may be made non-uniform around the periphery of the stoma 12. For example, the sealing force may be reduced in a certain region to create one or more preferential leak paths. Additionally or alternatively, the sealing force may be increased in a certain region that is known to be vulnerable to leakage. In contrast, the inflatable bag 10 of FIG. 1 generally applies a uniform sealing pressure across the entire contact area between the inflatable bag 10 and the stoma 12. The sealing pressure corresponds to the inflation pressure of the inflatable bag 10, and is uniform throughout the volume of the inflatable bag 10.

If desired, the stoma seal 22 (or at least a portion of the stoma seal 22) may be permeable to gas. In that case, the flatus passes through the stoma seal 22 into a region 30 immediately behind the stoma seal 22. In contrast, in the appliance 8 of FIG. 1, the membrane portion 10a of the inflatable bag 10 in contact with the stoma 12 is necessarily impermeable (e.g., gas may not pass entirely through the material of the inflatable bag 10) so as to contain the inflation fluid. In order to vent flatus emanating from the stoma 12, the flatus has to vent around the periphery of the inflatable bag 10; the flatus has to pass laterally at the interface between the inflatable bag 10 and the stoma 12, in order to vent around the periphery of the inflatable bag 10.

Whether or not the tensioned stoma seal 22 of FIG. 2 is permeable to gas, the region 30 behind the stoma seal 22 is used to house a deodorizing filter 32 for deodorizing vented flatus. If the stoma seal 22 is (at least partly) permeable, flatus may pass directly into the region 30, and vent through the deodorizing filter 32 to a vent port (not shown). If the stoma seal 22 is impermeable (or only partly permeable), then flatus passes alternatively (or additionally) around the periphery of the stoma seal 22 to the region 30, and vent through the deodorising filter 32 to the vent port (not shown).

In contrast, in the appliance 8 of FIG. 1, the inflatable bag 10 occupies a significant portion of the available volume behind the membrane in contact with the stoma 12, and makes it impractical to locate a deodorizing filter in this region, or it may require careful design to accommodate a deodorizing filter without increasing the size of the appliance unnecessarily.

A further feature of the tensioned stoma seal 22 of FIG. 2 is that a tensioning structure (not shown) for applying tension to the stoma seal 22 is distinct from the stoma seal 22, and does not contact the stoma 12. The tensioning structure is separable from the stoma seal 22 (for example, see FIG. 3), and may be re-usable with a replacement stoma seal 22. The tensioning structure may be tailored or customised to the shape of the individual's stoma 12, and is a reusable device, which provides significant cost efficiencies.

In contrast, in the appliance 8 of FIG. 1, the inflatable bag 10 is in intimate contact with the stoma 12, and needs to be replaced entirely by a new inflatable bag 10 whenever the user desires a fresh stoma seal.

Figure 3:
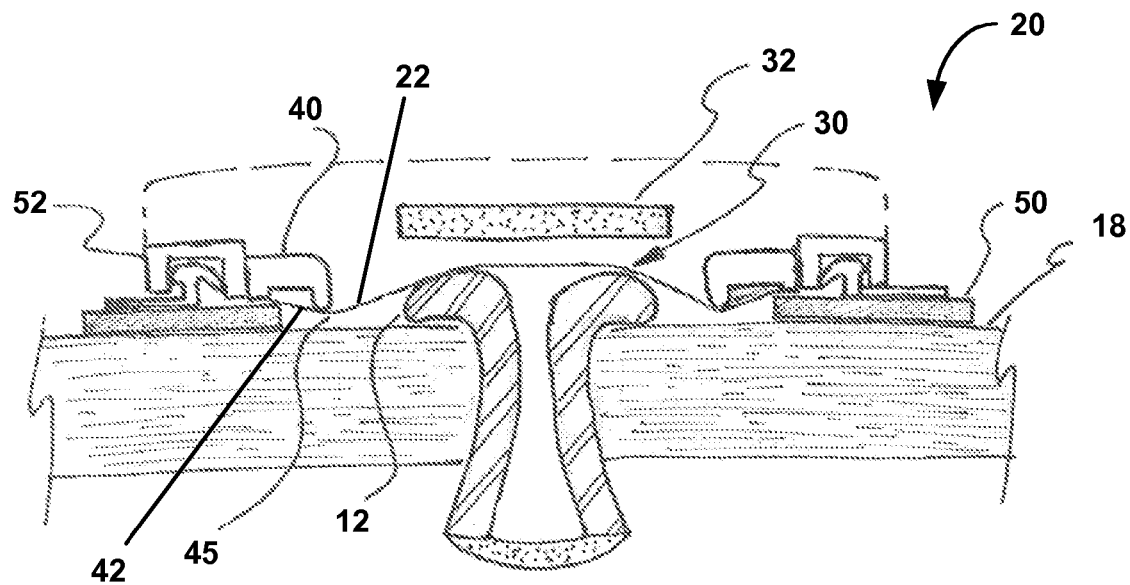
FIG. 3 is a schematic cross sectional view of an embodiment of a controlled evacuation ostomy appliance with a tensioned stoma seal.

Referring to FIG. 3, the appliance 20 further comprises a tensioning structure 40 for applying the tension to the stoma seal 22 as explained hereinbefore. The tensioning structure 40 applies tension at a position 42 which, in use, is (i) outboard of the periphery of the stoma 12, and (ii) is closer to the surface of the peristomal skin 18 than is the most projecting part of the stoma 12.

Figure 5A:
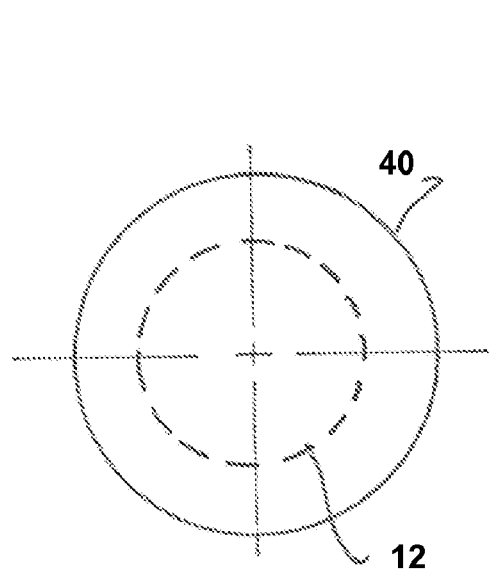
FIG. 5A is a schematic plan view of a tension applying structure having a circular shape.
Figure 5B:
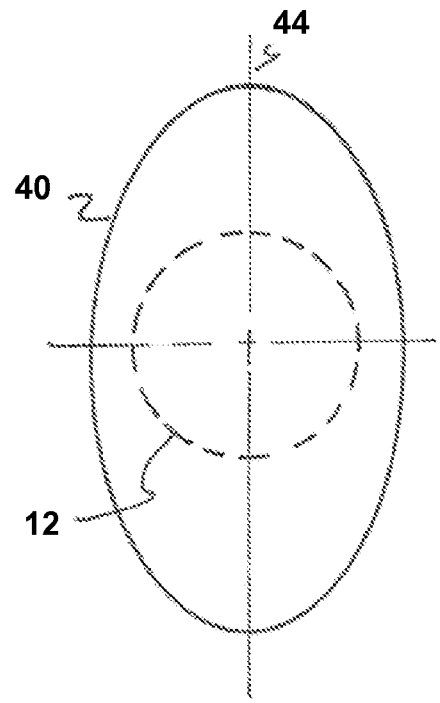
FIG. 5B is a schematic plan view of a tension applying structure having an oval shape.

Referring to FIGS. 5A and 5B, the tensioning structure 40 has a closed loop configuration. Referring to FIG. 5A, the tensioning structure 40 has a generally circular configuration. A circular configuration is useful to provide a generally wrinkle-free and/or generally uniform tension to the stoma seal 22. Alternatively, the tensioning structure 40 may have a generally non-circular configuration. A non-circular configuration may be useful to provide a non-uniform sealing tension in the stoma seal 22. For example, referring to FIG. 5B, the non-circular configuration may be symmetrical, for example, oval (or elliptical, or egg-shaped, or another similar shape). The oval configuration of the tensioning structure 40 may, for example, be used with a major axis 44 arranged in the vertical direction (when the ostomate is standing upright). Such an arrangement creates a slightly lower sealing force on the lower part of the stoma 12, such that any accidental leakage will occur downwardly rather than sideways (laterally). Similar principles may, of course, be applied to increase the sealing pressure at points known to be vulnerable to leakage.

Figure 4:
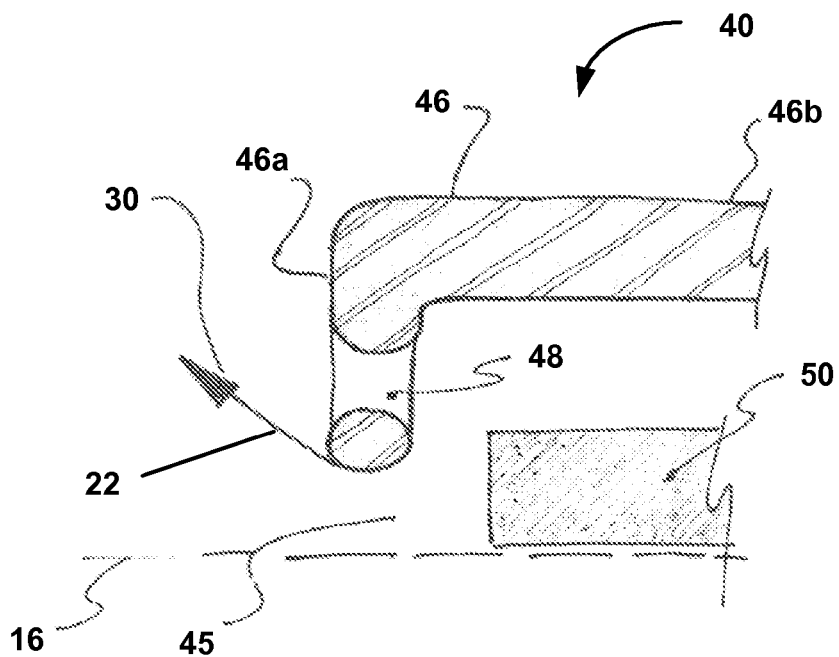
FIG. 4 is a schematic cross sectional detailed view of the tension applying structure of FIG. 3.

Referring to FIGS. 3 and 4, the tensioning structure 40 holds the edge of the stoma seal 22 such that, at least at one position around the periphery of the stoma seal 22, a clearance 45 exists between the periphery of the stoma seal 22 and the peristomal skin 18. The clearance 45 exists at one or more small regions, or over one or more significant sectors, or around the entire periphery of the stoma seal 22. The clearance 45 provides an escape path for any feces that leak between the stoma seal 22 and the stoma 12 to be directed away, so as not to be trapped and risk affecting the future integrity of the stoma seal 22.

The tensioning structure 40 may have a variety of different possible shapes or configurations. In the form illustrated in FIG. 3 (and shown in more detail in FIG. 4), the tensioning structure comprises a wall or rib 46 having a distal portion 46*a* for mounting, or bearing against, the stoma seal 22, and a proximal portion 46*b* for supporting the distal portion 46*a*. The proximal portion 46*b* is angled with respect to the distal portion 46*a*. One or more apertures 48 may be provided in the wall 46, for example, near or at the distal portion 46*a*. The aperture(s) 48 enables flatus venting between the stoma 12 and the stoma seal 22 to pass to the region 30 behind the stoma seal 22, in which a deodorizing filter 32 (not shown in FIG. 4) may be located.

Figure 6:
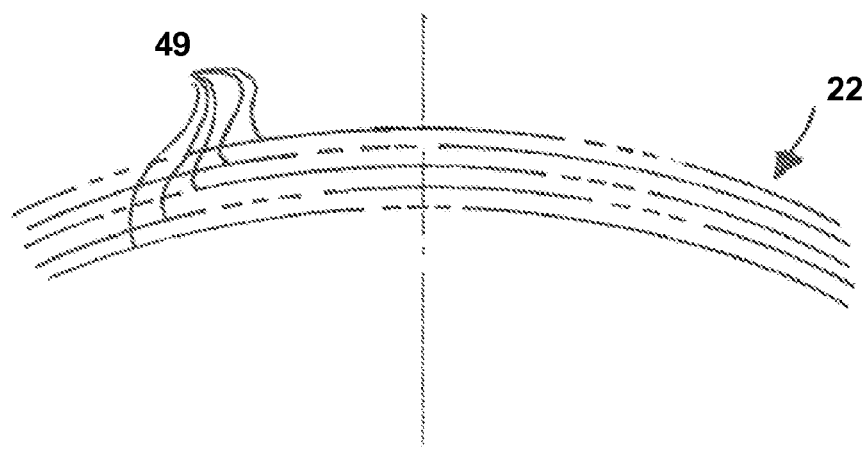
FIG. 6 is a schematic view of a seal membrane having plural layers.
Figure 7A:
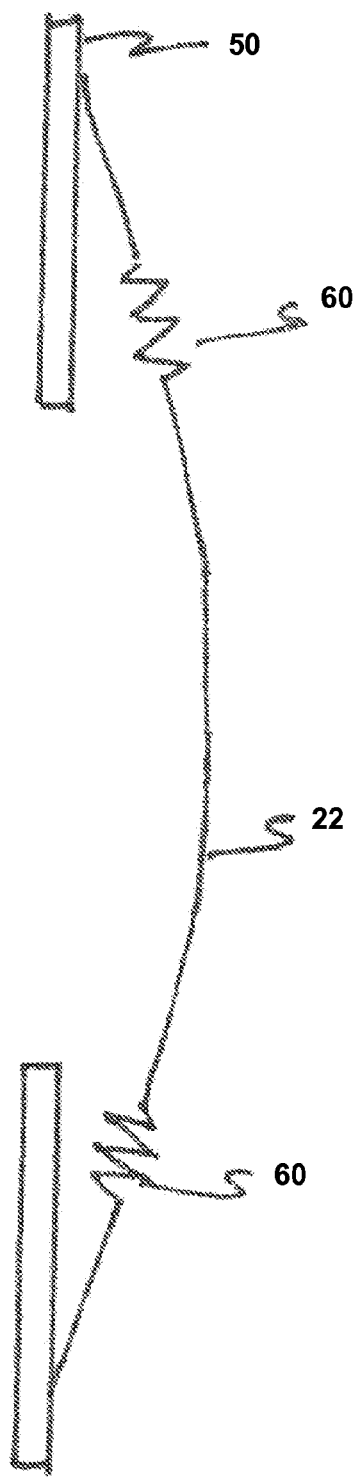
FIG. 7A is a schematic cross sectional view of a tensioned stoma seal with a tension limiter.
Figure 7B:
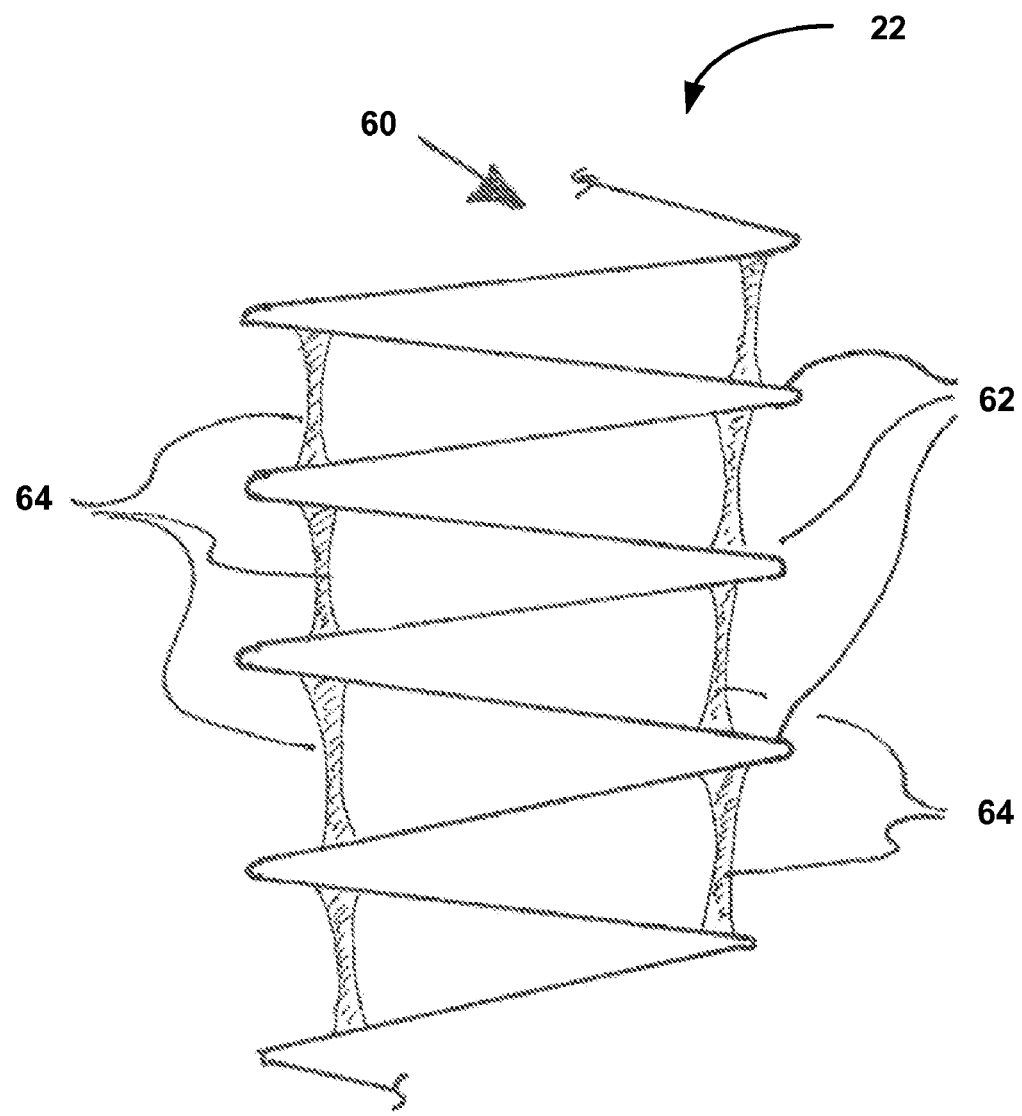
FIG. 7B is a schematic cross sectional view of the tension limiter of FIG. 7A in more detail.

The stoma seal 22 may be impermeable, or at least a portion of the stoma seal 22 may be gas-permeable (e.g., in the sense that flatus from the stoma 12 passes from one side of the stoma seal 22 to the other). By way of example only, permeability may be achieved by:

(a) including in the stoma seal 22 a region of open cell foam, or an activated carbon filter;

(b) including in the stoma seal 22 a gas-permeable membrane, such as expanded PTFE (e.g., in foam form), which may be especially effective at holding back liquid because it is hydrophobic;

(c) having the stoma seal 22, as shown in FIG. 6, include a plurality of interleaved membranes 49 which define a narrow and tortuous vent path for gas between successive layers, for example, by having non-overlapping perforated sections in each layer which may be composed of hydrophobic material or carry a hydrophobic coating; and/or (d) perforating the membrane with a plurality of holes, which could be created, or example, by a laser perforation process, of sufficiently large number and appropriate size to allow passage of gas through the membrane but prevent passage of effluent.

The tensioning structure 40 is held, in use with respect to the wearer's body, by a support 50. The support takes a variety of forms, for example, a belt or garment worn on the body, and/or a device secured to the skin, for example, by adhesive. In the embodiment of FIG. 3, the support 50 is an adhesive wafer having a stomal aperture. The stomal aperture aligns with the stomal aperture of the appliance 20. The tensioning structure 40 is mounted directly or indirectly on the support 50. The tensioning structure 40 may be removably mounted on the support 50, for example, by a mechanical coupling 52 similar to a mechanical ostomy coupling. Such a coupling 52 enables the tensioning structure 40 to be dismantled, and re-used with a new stoma seal 22. Alternatively, if it is desired to embody the appliance 20 as a disposable one-piece item, the tensioning structure 40 might not be designed to be removable from the support 50.

The tensioning structure 40 may have a fixed, or predetermined (i.e., non variable) position relative to the support. For example, the tensioning structure 40 may be fixed by adhesive or by a mechanical clamp which does not allow position adjustment. Alternatively, the tensioning structure 40 may be movable relative to the support 50. For example:

(a) The tensioning structure 40 may be movable by manual adjustment or setting, e.g., by hand and/or by using a suitable adjustment/setting tool.

For example:

(i) the tensioning structure 40 may be movable rotatably (e.g., angularly) relative to the stoma 12 and/or the support 50. Such rotatable movement is suitable for fine-tuning the tension in the stoma seal 22, by creating tension in an angular direction; or (ii) the tensioning structure 40 may be adjustable by means of a force-limiting retaining system, such as one or more torque nuts having threads designed to slip when the torque exceeds a certain threshold;

(b) The tensioning structure 40 may be positioned by, or include, an automatic tensioning system, such as a constant force spring, e.g., a coil spring, and a Euler beam spring, which applies a predetermined tension to the stoma seal 22.

In any of the above fixed, or variable, position arrangements, the stoma seal 22 is configured to limit the tension within the seal membrane itself. For example, referring to FIGS. 7A and 7B, the stoma seal 22 comprises a plurality of frangible folds 60. The folds 60 are located near an outer periphery of the stoma seal 22. The frangible folds 60 include concertina folds 62 that are held by frangible joins 64 intended to break when the tension reaches a certain threshold. As the seal membrane 22 is stretched, successive frangible joins 64 break, thus elongating the membrane slightly, and keeping the stoma seal 22 tension below the threshold.

Other techniques for regulating the tension in the stoma seal 22 may include multiple layers of membrane 49 (FIG. 6) which are joined together with multiple frangible joints, or a frangible net-like structure containing a membrane that is slack. The tension is borne by the net-like structure, while the seal characteristics are provide by the membrane.

Figure 8:
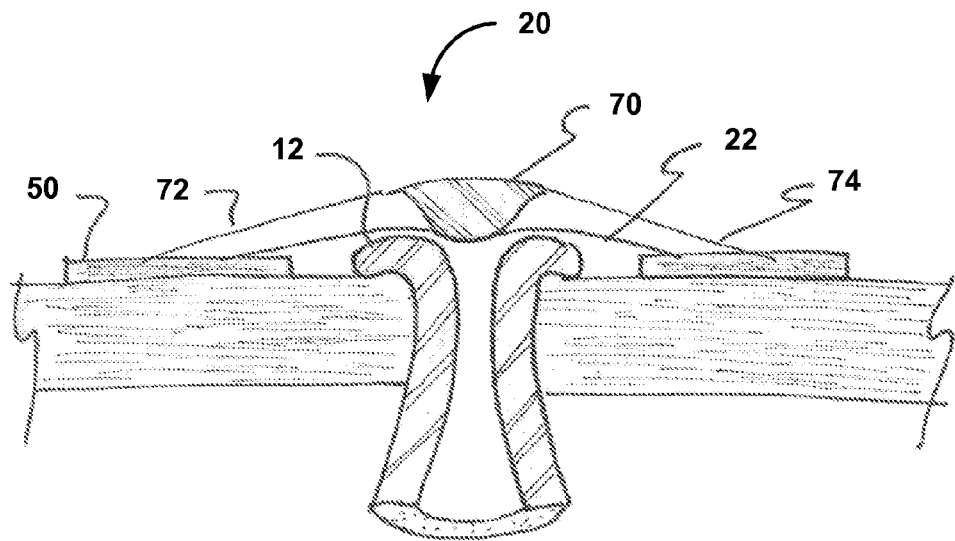
FIG. 8 is a schematic cross sectional view of a tensioned stoma seal with a shape defining member.
Figure 9:
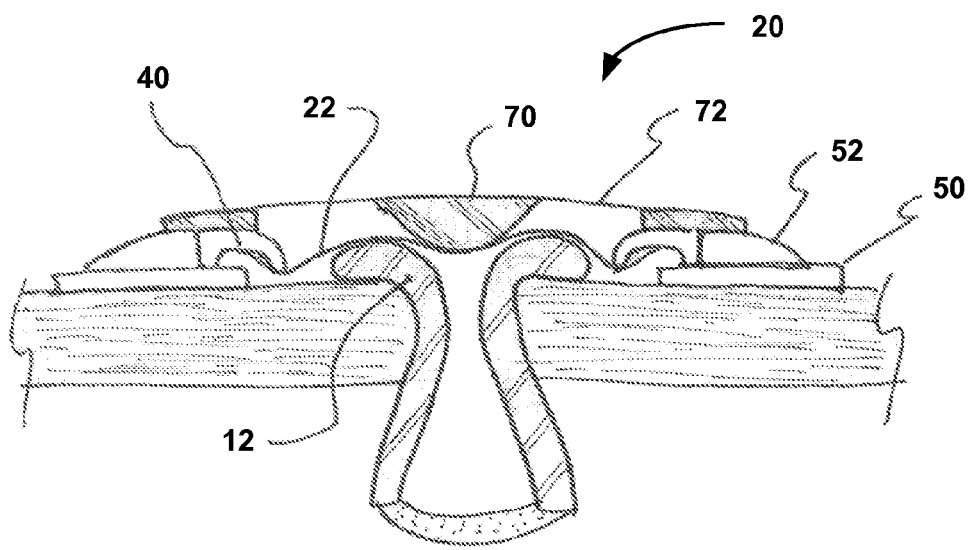
FIG. 9 is a schematic cross sectional view of a tensioned stoma seal with an additional shape defining member.

Referring to FIGS. 8 and 9, the appliance 20 may further comprise one or more shape defining members 70 for controlling the shape of the stoma seal 22. For example, a centrally disposed shape defining member 70 is provided on the side of the stoma seal 22 facing away from the stoma 12. The shape defining member 70 has a projecting shape to press the stoma seal 22 to partly enter the mouth of a stoma 12. Such a shape increases the contact area between the stoma seal 22 and the stoma 12, to enhance the seal characteristics. The shape defining member 70 may be of an at least partly conformable material, to avoid local pressure points. For example, the shape defining member 70 may be:

(a) a bag that is inflatable or pre-inflated using a suitable inflation fluid (gas or liquid);

(b) an elastic foamed polymer;

(c) a resilient solid material, such as silicone rubber;

(d) a moldable material, such as foamed PTFE, a viscoelastic foam, or a loose bag containing loose particles such as small balls or beads; or (e) a custom shaped object that has been cut of molded to fit the shape of the wearer's stoma 12.

The appliance 20 may further comprise a support 72 for supporting the shape defining member 70. The support 72 may be movable, or it may be fixed. For example, referring to FIG. 8, the support 72 comprises a second tensioned membrane 74 behind the stoma seal 22. The second tensioned membrane 74 is mounted independently of the stoma seal 22, to allow independent setting of the tension in the second tensioned membrane 74, and thus provide independent setting of the pressing force applied by the shape defining member 70 compared to the force applied by the tension in the stoma seal 22. Alternatively, the second tensioned membrane 74 may be mounted with the stoma seal 22.

Referring to FIG. 9, the support 72, alternatively, includes an outer cap, or other support more rigid than a tensioned membrane, for directly pressing against the shaped defining member 70.

Figure 10:
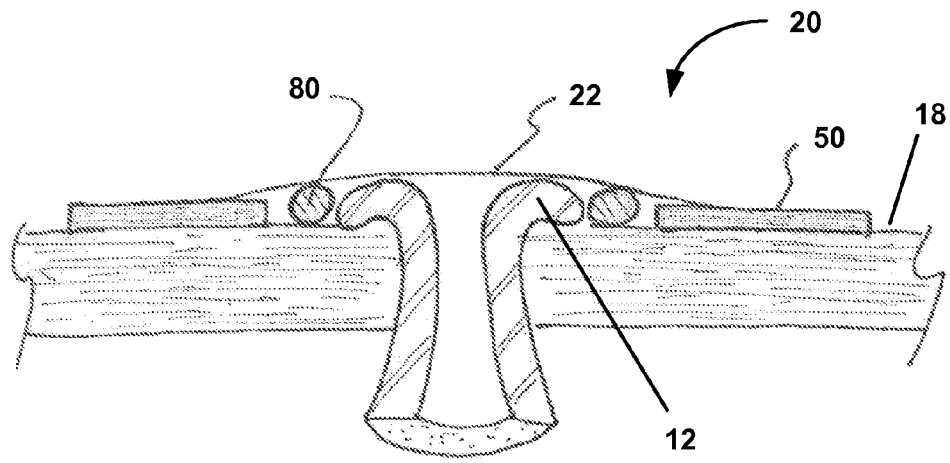
FIG. 10 is a schematic cross sectional view of an additional tensioned seal membrane with a shape defining member arranged on the stoma-facing face.

Referring to FIG. 10, the appliance 20 further includes a peristomal gasket 80 arranged between the stoma seal 22, and the wearer's peristomal skin 18 or stoma 12. For example, the peristomal gasket 80 is of closed-loop shape, for enhancing the seal characteristics in the peristomal region of the skin, and to obstruct leakage between the adhesive of the support 50, and the peristomal skin 18. Such a peristomal gasket 80 may be carried by the stoma seal 22, or it may be supported independently, for example, by the support 50.

Figure 11:
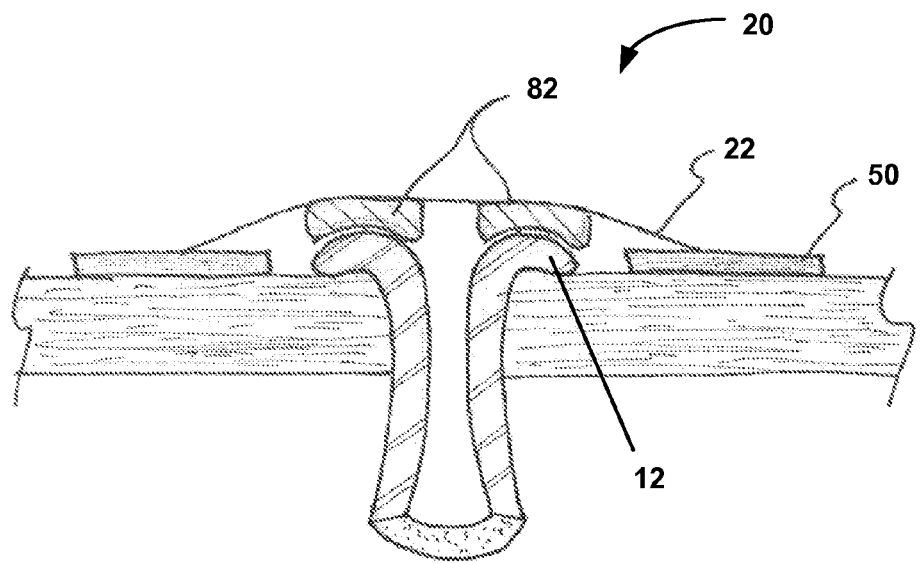
FIG. 11 is a schematic cross sectional view of additional shape defining members arranged on the stoma-facing face of the tensioned seal membrane.

Referring to FIG. 11, the appliance 20 further includes a supplementary sealing member 82 for contacting the stoma 12. The sealing member 82 is carried by the stoma seal 22 on its face facing towards the stoma 12. For example, the sealing member 82 may include an inflatable, or inflated chamber to ensure a uniform contact force applied to the stoma 12; or a closed loop (e.g., circular) piece of closed-cell foam; or one or more concentric arrangements of ridges to form local ring seals. Such plural rings may act as successive seals in the case of leakage outward from the stoma 12.

Although many of the foregoing embodiments illustrate features of the appliance in isolation, it is certainly within the scope of this invention that some of the above features may be used together.

We claim:

1. A controlled evacuation ostomy appliance for controlling the discharge from a wearer's stoma comprising:
   a. a frame attachable to the wearer and positionable around the stoma, said frame having a stomal aperture;
   b. a flexible film-like membrane located inside said frame and extending across at least part of the stomal aperture, said membrane being configured for contacting the stoma and for obstructing the discharge of at least solid body waste therefrom; and
   c. tensioning means for applying tension to said membrane, said tensioning means securing said membrane to said frame and having a closed loop shape, said tensioning means being secured to said membrane radially outside the stoma's periphery and between peristomal skin and upper surface of the stoma, said tensioning means applying tension to said membrane by drawing the membrane into a concave configuration around the stoma by pulling said membrane against the stoma so as to obstruct discharge from the stoma.

2. The controlled evacuation ostomy appliance according to claim 1, wherein the tensioning means is adjustable for adjusting the magnitude of the tension in the membrane.

3. The controlled evacuation ostomy appliance according to claim 1, wherein the membrane is not under substantial tension prior to fitting to a stoma, the membrane being configured such that entry of the stoma into the stomal aperture presses against the membrane in such a manner that the tensioning means and stoma together tension the membrane.

4. The controlled evacuation ostomy appliance according to claim 1, wherein said tensioning means has a shape selected from: circular; and non-circular.

5. The controlled evacuation ostomy appliance according to claim 1, further comprising a deodorizing filter on the opposite side of the membrane to the stomal aperture.

6. The controlled evacuation ostomy appliance according to claim 1, wherein at least a portion of the membrane is gas-permeable to allow flatus to pass from the stoma through the membrane.

7. The controlled evacuation ostomy appliance according to claim 6, wherein the permeable portion of the membrane comprises a phase separator allowing gas to pass therethrough while obstructing the passage of solid) and/or liquid body waste.

8. The controlled evacuation ostomy appliance according to claim 7, wherein the phase separator comprises one or more selected from: an activated charcoal filter; open cell foam; an expanded PTFE block; and a composite membrane comprising multiple layers defining a tortuous gas flow path therethrough.

9. The controlled evacuation ostomy appliance according to claim 1, wherein the membrane comprises a tension limiter.

10. The controlled evacuation ostomy appliance according to claim 9, wherein the tension limiter comprises a frangible support for holding the membrane in an artificially contracted state, such that upon the tension reaching a breaking threshold, the frangible connection breaks to release the artificially contracted state of the membrane.

11. The controlled evacuation ostomy appliance according to claim 9, wherein the tension limiter comprises a constant force spring member.

12. The controlled evacuation ostomy appliance according to claim 1, further comprising a shape defining member for pressing against the membrane on the opposite side to the stoma, for defining a shape that is not possible by applying tension alone.

13. The controlled evacuation ostomy appliance according to claim 12, wherein the shape defining member comprises a projection for defining a central bulge in the membrane for at least partly entering the mouth of the stoma.

14. The controlled evacuation ostomy appliance according to claim 13, further comprising a support for the shape defining member.

15. The controlled evacuation ostomy appliance according to claim 14, wherein the support comprises a second tensioned membrane.

16. The controlled evacuation ostomy appliance according to claim 1, further comprising a releasable coupling for enabling the tensioning device to be detachable.

* * * * *